(12) United States Patent
Ivanova et al.

(10) Patent No.: US 7,850,952 B2
(45) Date of Patent: Dec. 14, 2010

(54) HAIR TREATMENT COMPOSITIONS

(75) Inventors: Katya Ivanova, Bebington (GB); Stuart Keith Pratley, Bebington (GB)

(73) Assignee: Conopco, Inc., Englewood Cliffs, NJ (US)

( * ) Notice: Subject to any disclaimer, the term of this patent is extended or adjusted under 35 U.S.C. 154(b) by 1199 days.

(21) Appl. No.: 10/550,623

(22) PCT Filed: Feb. 11, 2004

(86) PCT No.: PCT/EP2004/001410

§ 371 (c)(1),
(2), (4) Date: Jun. 27, 2006

(87) PCT Pub. No.: WO2004/084846

PCT Pub. Date: Oct. 7, 2004

(65) Prior Publication Data

US 2006/0263314 A1 Nov. 23, 2006

(30) Foreign Application Priority Data

Mar. 24, 2003 (EP) .................................. 03251827

(51) Int. Cl.
*A61Q 5/06* (2006.01)
(52) U.S. Cl. ..................... 424/70.12; 424/47
(58) Field of Classification Search ........................ None
See application file for complete search history.

(56) References Cited

U.S. PATENT DOCUMENTS

| | | | | |
|---|---|---|---|---|
| 2,736,721 | A | 2/1956 | Dexter | 260/42 |
| 2,814,601 | A | 11/1957 | Currie et al. | 260/29.1 |
| 4,693,935 | A | 9/1987 | Mazurek | 428/352 |
| 4,728,571 | A | 3/1988 | Clemens et al. | 428/352 |
| 4,988,779 | A | 1/1991 | Medford et al. | 525/478 |
| 5,021,477 | A | 6/1991 | Garbe et al. | 424/70 |
| 5,166,275 | A | 11/1992 | Enomoto et al. | 525/327.7 |
| 5,166,276 | A | 11/1992 | Hayama et al. | 525/329 |
| 5,330,747 | A | 7/1994 | Krzysik | 424/63 |
| 5,451,610 | A * | 9/1995 | Krzysik | 424/63 |
| 5,667,771 | A | 9/1997 | Carballada et al. | 424/70.12 |
| 5,674,478 | A * | 10/1997 | Dodd et al. | 424/70.1 |
| 5,776,444 | A | 7/1998 | Birtwistle et al. | 424/70.12 |
| 5,911,979 | A | 6/1999 | Midha et al. | 424/70.12 |
| 5,980,876 | A | 11/1999 | Peffly | 424/70.12 |
| 6,113,883 | A | 9/2000 | Midha et al. | 424/47 |
| 6,165,455 | A | 12/2000 | Torgerson et al. | 424/70.12 |
| 6,248,316 | B1 | 6/2001 | Peffly et al. | 424/70.12 |
| 6,280,765 | B1 | 8/2001 | Gueret | 424/449 |
| 6,350,439 | B1 | 2/2002 | Dupuis | 424/70.12 |
| 6,787,130 | B2 * | 9/2004 | Dhamdhere et al. | 424/70.12 |
| 6,887,859 | B2 * | 5/2005 | Clapp et al. | 514/60 |
| 2002/0018790 | A1 | 2/2002 | Vatter et al. | 424/401 |
| 2002/0018791 | A1 | 2/2002 | Vatter et al. | 424/401 |

FOREIGN PATENT DOCUMENTS

| | | |
|---|---|---|
| EP | 0 240 350 | 10/1987 |
| EP | 0 408 311 | 1/1991 |
| EP | 0 412 704 | 2/1991 |
| EP | 0 412 707 | 2/1991 |
| EP | 412 707 | 2/1994 |
| EP | 412 704 | 4/1999 |
| EP | 408 311 | 10/2006 |
| WO | 93/03704 | 3/1993 |
| WO | 93/23446 | 11/1993 |
| WO | 95/00106 | 1/1995 |
| WO | 95/04518 | 2/1995 |
| WO | 95/32703 | 12/1995 |
| WO | 96/32918 | 10/1996 |
| WO | 98/48776 | 10/1998 |
| WO | 98/48770 | 11/1998 |
| WO | 98/51261 | 11/1998 |
| WO | 98/51755 | 11/1998 |
| WO | WO 01/08644 | * 2/2001 |
| WO | 03/028677 | 4/2003 |

OTHER PUBLICATIONS

Co-pending Application: Applicant: Ivanova et al., U.S. Appl. No. 10/550,622; Filed: Sep. 23, 2005.
Flick, "*Cosmetic and Toiletry Formulations*", Noyes Publications, 2nd Edition, vol. 1, 1989, pp. 392-393.
European Search Report in EP application EP 08 15 8467.
Flick, "*Cosmetic and Toiletry Formulations*", vol. 1, 2nd Edition, 1969, pp. 392-393.

* cited by examiner

*Primary Examiner*—Jyothsna A Venkat
(74) *Attorney, Agent, or Firm*—Karen E. Klumas

(57) ABSTRACT

A mousse, cream, lotion or spray leave on hair treatment composition comprising a silicone pressure sensitive adhesive.

8 Claims, No Drawings

HAIR TREATMENT COMPOSITIONS

FIELD OF THE INVENTION

This invention relates to leave on hair treatment compositions and to their use in the treatment of hair.

BACKGROUND AND PRIOR ART

One of the most common methods for styling hair has been applying fixative agents to the hair, such as high molecular weight polymers. The problem with using such fixative agents is that they have a tendency to make the hair feel sticky, stiff and crisp. Furthermore conventional fixative agents also tend to make consumers hands feel sticky when they are applying or styling their hair with compositions containing them.

One way in which this problem has been addressed in the past has been to include conditioning agents, for example silicones and cationic surfactants, in the compositions, to counter the negative effects of the styling agents. Although such conditioning agents do provide substantial improvements in for example the wet and dry combing properties of the hair and in the smoothness of the hair, they tend to have a negative effect on the styling of hair e.g. poor style creation and hold. Furthermore the use of conditioners does not overcome the sticky feeling on consumers hands during application and styling with the product.

The present invention provides high styling efficacy (e.g. control, ease of styling, style longevity and manageability) without undue stiffness and sticky feel.

Pressure sensitive adhesives (PSAs) have been used in hair care compositions as described in U.S. Pat. No. 5,166,276, EP408311, EP412707 and EP412704. However these PSAs tend to hydrolyse in aqueous and hydroalcoholic hair care products.

The present invention has the added advantage that hair can be styled without the consumers hands becoming sticky.

A further advantage is that hair styled with compositions of the present invention does not become limp or lose its style or curl retention in humid conditions.

The invention also relates to PSAs which are particularly stable in aqueous and hydroalcoholic hair care products.

SUMMARY OF THE INVENTION

Accordingly, this invention provides a mousse, cream, lotion, tonic or spray leave on hair treatment composition comprising a silicone pressure sensitive adhesive present as an emulsion.

This invention provides for the use of silicone PSA's as defined herein in a hair treatment composition to impart styling without compromising feel, especially omitting stickiness, on hair and hands.

A method for styling hair is also described which comprises contacting the hair with the composition described above.

DETAILED DESCRIPTION OF THE INVENTION

Unless specified otherwise, all wt % values quoted hereinafter are percentages by weight based on total weight of the hair treatment composition.

By "insoluble" is meant that the material is not soluble in water (distilled or equivalent) at a concentration of 0.1%, at 25° C.

Silicone Pressure Sensitive Adhesives

This present invention relates to the use of silicone PSAs for hair care applications.

The term "silicone pressure sensitive adhesive" (SPSA) refers to pressure sensitive adhesives comprising a silicone resin and a polydiorganosiloxane. These "pressure sensitive adhesive" (PSA) materials are permanently tacky at room temperature and able to develop measurable adhesion to a surface simply upon contact or by the application of a light pressure. Generally they do not require heat. No chemical reaction takes place between the adhesive and the adherent, no curing of the adhesive is necessary and no solvent is required to be lost during the adhesion process. In the context of the present invention there are 3 types of silicone PSAs:

i) One class of silicone pressure sensitive adhesives consists of a mixture of (i) a silanol end-blocked polydiorganosiloxane fluid, e.g. a polydimethylsiloxane polymer and (ii) a trimethylsilyl end-blocked polysilicate resin such as a silicate resin consisting of a benzene-soluble resinous copolymer containing silicon-bonded hydroxyl radicals and consisting essentially of triorganosiloxy units of the formula $R_3SiO_{1/2}$ and tetrafunctionalsiloxy units of the formula $SiO_{4/2}$ in a ratio of about 0.6 to 0.9 triorganosiloxy units for each tetrafunctionalsiloxy unit present in the copolymer, wherein each R is a monovalent organic radical independently selected from the group consisting of hydrocarbon radicals of from 1 to 6 inclusive carbon atoms. U.S. Pat. No. 2,736,721 to Dexter et al. and U.S. Pat. No. 2,814,601 to Currie et al. teach such or similar silicone pressure sensitive adhesives.

ii) A preferred class of silicone PSAs are prepared by condensing the silicone fluid and the silicate. In this preferred condensation reaction, the silicate resin and the silicone fluid are mixed together in the presence of a catalytic amount of a silanol condensation catalyst and then the silicate resin and the silicone fluid are condensed, for example, by heating under reflux conditions for 1 to 20 hours. Examples of silanol condensation catalysts are primary, secondary and tertiary amines, carboxylic acids of these amines and quaternary ammonium salts.

iii) A further optional step can also employ an alkenyl-functional polymer and a crosslinking agent containing silicone-bonded hydrogen atoms, they are cured by a hydrosilation addition reaction using a platinum-type catalyst as described in U.S. Pat. No. 4,988,779. In such systems the molar ratio of silicon bonded hydrogen groups to silicone bonded alkenyl groups is typically greater than 1. However these systems are not highly preferred.

A preferred silicone PSA comprises (a) 40 to 70 parts by weight of at least one silicone copolymer resin and (b) 30 to 60 parts by weight of at least one polydiorganosiloxane. The silanol content of the silicone pressure sensitive adhesive composition is reduced by chemically treating at least a portion of (a), (b) or the mixture of (a) and (b) with at least one chemical treating agent (c) that reacts with silicon-bonded hydroxyl groups to reduce the silicon-bonded hydroxyl content of the composition.

Preferably the silicon-bonded hydroxyl content of the composition is reduced to a range of between 8000 and 13,000.

The silicone resin copolymers (i) usually contain silicon-bonded hydroxyl radicals in amounts which typically range from about 1 to 4 weight percent of silicon-bonded hydroxyl radicals and comprise triorganosiloxy units of the formula $R_3SiO_{1/2}$ and tetrafunctional siloxy units of the formula $SiO_{4/2}$ in a mole ratio of from 0.6 to 0.9 $R_3Si_{1/2}$ units for each SiO 4/2 unit present. Blends of two or more such copolymers may also be used. There should be at least some and preferably at least 0.5% silicon-bonded hydroxyl content to enable the polydiorganosiloxane component to copolymerize with the copolymer resin and/or to react with the end blocking agent being added to chemically treat the silicone pressure-sensitive adhesive composition. Each R denotes, independently, a monovalent hydrocarbon radical having from 1 to 6 inclusive carbon atoms such as methyl, ethyl, propyl, isopropyl, hexyl, cyclohexyl, vinyl, allyl, propenyl and phenyl. Preferably, the R 3 SiO 1/2 units are Me 3 SiO 1/2 units and/or Me 2 R 1 SiO 1/2 units wherein is R 1 is a vinyl ("Vi") or phenyl ("Ph") radical. More preferably, no more than 10 mole percent of the R 3 SiO 1/2 units present in resin copolymer (i) are Me 2 R 2 SiO 1/2 units and the remaining units are Me 3 SiO 1/2 units where each R 2 is a vinyl radical. Most preferably, the R 3 SiO 1/2 units are Me 3 SiO 1/2 units.

The preferred class of silicone PSAs (ii) usually comprise one or more polydiorganosiloxanes comprising ARSiO units terminated with endblocking TRASiO 1/2 units, where each R is as defined in the paragraph above. Each A radical is selected from radicals such as R or halohydro-carbon radicals of from 1 to 6 inclusive carbon atoms such a chloromethyl, chloropropyl, 1-chloro-2-methylpropyl, 3,3,3-trifluoropropyl and $F_3C(CH_2)_5$ radicals. Thus the polydiorganosiloxane can contain $Me_2SiO$ units, PhMeSiO units, MeViSiO units, $Ph_2SiO$ units, methylethylsiloxy units, 3,3,3-trifluoropropyl units and 1-chloro, 2-methylpropyl units and the like. Preferably, the ARSiO units are selected from the group consisting of $R_2SiO$ RR'SiO units, $Ph_2SiO$ units and combinations of both where R and R' are as for R in the paragraph above, at least 50 mole percent of the R' radicals present in the polydiorganosiloxane (ii) are methyl radicals and no more than 50 mole percent of the total moles of ARSiO units present in each polydiorganosiloxane of (ii) are $Ph_2SiO$ units. More preferably, no more than 10 mole percent of the ARSiO units present in each polydiorganosiloxane (ii) are MeRSiO units where R is as above defined and the remaining ARSiO units present in each polydiorganosiloxane are $Me_2SiO$ units. Most preferably, substantially all of the ARSiO units are $Me_2SiO$ units. Each T radical is R, OH, H or OR' radicals where each R' is an alkyl radical of from 1 to 4 inclusive carbon atoms such as methyl, ethyl, n-propyl, and isobutyl radicals. H, OH and OR' provide a site for reaction with the endblocking triorganosilyl units of ingredient (iii) and also provide a site for condensation with other such radicals on polydiorganosiloxanes (ii) or with the silicon-bonded hydroxyl groups present in resin copolymer (i). Use of polydiorganosiloxanes where T is OH is most preferred because the polydiorganosiloxane (ii) can then readily copolymerize with the resin copolymer (i). When an appropriate catalyst such as HCl, which is generated when chlorosilanes are used, or ammonia, which is generated when organosilazanes are used, as endblocking agents, then triorganosiloxy (e.g., R 3 SiO 1/2 such as $(CH_3)_3SiO$ 1/2 or $CH_2CH(CH_3)_2SiO$ 1/2) unit terminated polydiorganosiloxanes can be employed because some of the triorganosiloxy units can be cleaved when the condensation reaction is conducted with heating. The cleavage exposes a silicon-bonded hydroxyl radical which can then condense with silicon-bonded hydroxyl radicals in the copolymer resin, with endblocking triorganosilyl units or with other polydiorganosiloxanes containing H, OH or OR' radicals or silicon-bonded hydroxyl radicals exposed by cleavage reactions. Mixtures of polydiorganosiloxanes containing different substituent radicals may also be used.

Each of the polydiorganosiloxanes (ii) preferably have a viscosity of from 100 centipoise to 30,000,000 centipoise at 25° C. (100 millipascal-seconds to 30,000 pascal seconds (Pa·s) where 1 centipoise equals 1 millipascal second). As is well-known, viscosity is directly related to the average number of diorganosiloxane units present for a series of polydiorganosiloxanes of varying molecular weights which have the same endblocking units. Polydiorganosiloxanes having a viscosity of from about 100 to 100,000 centipoise at 25° C. range from fluids to somewhat viscous polymers. These polydiorganosiloxanes are preferably pre-reacted with resin copolymer (i) prior to condensation in the presence of endblocking agent (iii) to improve the tack and adhesion properties of the resulting PSA as will be further described. Polydiorganosiloxanes having viscosities in excess of 100,000 centipoise can typically be subjected to the condensation/endblocking step (II) of the present invention without pre-reaction. Polydiorganosiloxanes having viscosities in excess of 1,000,000 centipoise are highly viscous products often referred to as gums and the viscosity is often expressed in terms of a Williams Plasticity value (polydimethylsiloxane gums of about 10,000,000 centipoise viscosity typically have a Williams Plasticity Value of about 50 mils (1.27 mm) or more at 25° C.).

Examples of endblocking agents (iii) are (Me3Si)2NH, (ViMe2Si)2NH, (MePhViSi)2NH, (CF3CH2CH2Me2Si) 2NH, (Me3Si)2NMe, (ClCH2Me2Si)2NH, Me3SiOMe, Me3SiOC2H5, Ph3SiOC2H5, (C2H5)3SiOC2H5, Me2PhSiOC2H5, (i-C3H7)3SiOH, Me3Si(OC3H7), MePh-ViSiOMe, Me3SiCl, Me2ViSiCl, MePhViSiCl, (H2CCHCH2)Me2SiCl, (n-C3H7)3SiCl, (F3CCF2CF2CH2CH2)3SiCl, NCCH2CH2Me2SiCl, (n-C6H13)3SiCl, MePh2SiCl, Me3SiBr, (t-C4H9)Me2SiCl, CF3CH2CH2Me2SiCl, (Me3Si)20, (Me2PhSi)20, BrCH2Me2SiOSiMe3, (p-FC6H4Me2Si)20, (CH3COOCH2Me2Si)20, [(H2CCCH3COOCH2CH2) Me2Si]20, [(CH3COOCH2CH2CH2)Me2Si]20, [(C2H5OOCCH2CH2)Me2Si]20, [(H2CCHCOOCH2) Me2Si]20, (Me3Si)2S, (Me3Si)3N, Me3SiNHCONHSiMe3, F3CH2CH2Me2SiNMeCOCH3, (Me3Si)(C4H9)NCON (C2H5)2, (Me3Si)PhNCONHPh, Me3SiNHMe, Me3SiN (C2H5)2, Ph3SiNH2, Me3SiNHOCCH3, Me3SiOOCCH3, [(CH3CONHCH2CH2CH2)Me2Si]20, Me3SiO(CH2) 40SiMe3, Me3SiNHOCCH3, Me3SiCCH, HO(CH2) 4Me2Si)20, (HOCH2CH2OCH2Me2Si)20, H2N(CH2) 3Me2SiOCH3, CH3CH(CH2NH2)CH2Me2SiOCH3, C2H5NHCH2CH2S(CH2)GMe2SiOC2H5, HSCH2CH2NH(CH2)4Me2SiOC2H5, HOCH2CH2SCH2Me2SiOCH3. Preferably, the endblocking agent employed is (Me3Si)2NH.

The PSAs described are emulsified.

A preferred silicone PSA emulsion can be prepared by mixing the silicone PSA in suitable solvents to give a dispersed phase. It is advantageous if this dispersed phase comprises 20 to 80% by weight of the silicone pressure sensitive adhesive. Preferably at least one solvent will be a volatile solvent, meaning a solvent with a boiling point below 300° C. One or more of the solvents is preferably a silicone. The PSA/solvent mixture is optionally emulsified in water using one or more surfactants. The preferred surfactants are anionic or nonionic surfactants, especially a blend of anionic and nonionic surfactants. The silicone solvent can be a linear polydiorganosiloxane such as hexamethyldisiloxane, octamethyltrisiloxane, decamethyltetrasiloxane, dodecamethylpentasiloxane or a polydimethylsiloxane of viscosity 1 cSt, or can be a cyclic siloxane such as decamethylcyclopentasiloxane or octamethylcyclotetrasiloxane or can be a mixture of one or more linear polydimethylsiloxanes with one or more cyclic siloxanes. Other solvents include ethyl acetate and hydrocarbons (e.g heptane, hexane, isododecane).

Hair Styling Polymer

The compositions of the invention may further comprise from 0.001% to 10% by weight of a hair styling polymer. More preferred amounts of hair styling polymer in the compositions of the invention are from 0.1% to 5% by weight of the composition, even more preferably from 0.5% to 3% by weight. However it is highly preferable if additional hair styling polymers they are not present or present in levels below 0.01 wt % of the total composition.

Hair styling polymers are well known. Suitable hair styling polymers include commercially available polymers that contain moieties that render the polymers cationic, anionic, amphoteric or nonionic in nature. Suitable hair styling polymers include, for example, block and graft copolymers. The polymers may be synthetic or naturally derived.

Examples of anionic hair styling polymers are:

copolymers of vinyl acetate and crotonic acid; terpolymers of vinyl acetate, crotonic acid and a vinyl ester of an alpha-branched saturated aliphatic monocarboxylic acid such as vinyl neodecanoate;

copolymers of methyl vinyl ether and maleic anhydride (molar ratio about 1:1) wherein such copolymers are 50% esterified with a saturated alcohol containing from 1 to 4 carbon atoms such as ethanol or butanol;

acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The additional styling polymer may also contain grafted silicone, such as polydimethylsiloxane.

Specific examples of suitable anionic hair styling polymers are:
RESYN® 28-2930 available from National Starch (vinyl acetate/crotonic acid/vinyl neodecanoate copolymer);
ULTRAHOLD® 8 available from BASF (CTFA designation Acrylates/acrylamide copolymer);
the GANTREZ®ES series available from ISP Corporation esterified copolymers of methyl vinyl ether and maleic anhydride);
Luviset PUR® available from BASF.

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are cross-linked silicone resins or gums. Specific examples include rigid silicone polymers such as those described in EP-A-0240350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic polymers are:
copolymers of N-vinylpyrrolidone and dimethylaminoethyl methacrylate, available from ISP Corporation as Copolymer 845, Copolymer 937 and Copolymer 958;
copolymers of N-vinylpyrrolidone and dimethylaminopropylacrylamide or methacrylamide, available from ISP Corporation as Styleze® CC10;
copolymers of N-vinylpyrrolidine and dimethylaminoethyl methacrylate;
copolymers of vinylcaprolactam, N-vinylpyrrolidone and dimethylaminoethylmethacrylate;
Polyquaternium-4 (a copolymer of diallyldimonium chloride and hydroxyethylcellulose);
Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;
Polyquaternium-16 (formed from methylvinylimidazolium chloride and vinylpyrrolidone), available from BASF as Luviquat® FC 370, FC 550, FC 905 and HM-552;
Polyquaternium-46 (prepared by the reaction of vinylcaprolactam and vinylpyrrolidone with methylvinylimidazolium methosulphate), available from BASF as Luviquat®Hold.

Examples of suitable naturally-derived polymers include shellac, alginates, gelatins, pectins, cellulose derivatives and chitosan or salts and derivatives thereof. Commercially available examples include Kytamer® (ex Amerchol) and Amaze® (ex National Starch).

Also suitable for use as additional styling polymers in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macrografted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

In certain embodiments of the invention, the styling polymer is preferably a copolymer having a backbone comprising a polyether and, depending from the backbone, a plurality of poly (vinyl ester) groups. At least some of the ester groups are hydrolysed to the corresponding alcohol, preferably at least 50%, more preferably at least 75%, most preferably at least 95% of the groups are hydrolysed to the corresponding alcohol. The poly (vinyl ester) chains optionally contain other functional groups in and/or on the polymer chain, such as, for example, amide and/or keto groups. The copolymer has a polyether backbone which is obtainable by the polymerisation of one or more alkylene oxides. The polyether may comprise a single alkyleneoxy group or a mixture of two or more alkyleneoxy groups. The polyether may, for example, be based on ethylene oxide, propylene oxide, butylene oxide, other alkylene oxides, polyglycerol and mixtures thereof. Optionally, the backbone comprises linkages other than those based on polyether, such as, for example, amide or keto linkages. Preferably, the copolymer comprises a polyethyleneglycol backbone. The copolymer is preferably polyethyleneglycol-co-polyvinylalcohol having polyvinylalcohol groups bound to the polyethyleneglycol i.e., substantially all of the poly (vinyl ester) groups are preferably hydrolysed in the copolymers used in the compositions of the invention. The copolymer can be produced by methods which are well-known to those skilled in the art. For example, the copolymers are obtainable by graft polymerisation. In a method comprising graft polymerisation, poly (vinyl ester) groups are preferably grafted onto a polyether and are subsequently hydrolysed to convert at least some of the ester groups to the corresponding alcohol. For example, DE 1 077 430, the contents of which are incorporated herein by reference, describes a process for the preparation of graft polymers of vinyl esters on polyalkylene glycols. The preparation of graft copolymers of polyvinyl alcohol on polyalkylene glycols by hydrolysis of the vinyl esters is described in DE 1 094 457 and DE 1 081 229, both also incorporated herein by reference. The weight average molecular weight of the polyether is preferably from 1 to 100 kDa. Preferred copolymers for use in compositions of the invention have a molar ratio of polyether to total poly (vinyl ester) and polyvinylalcohol groups in the range of from about 95:5 to 5:95, more preferably about 30:70 to about 50:50. Typically, such copolymers have a molar ratio of polyether to total poly(vinyl ester) and polyvinylalcohol groups of about 40:60. The copolymer may be non-cross-linked or cross-linked and it is preferred that the copolymer is cross-linked. Suitable cross-linking agents are those compounds which can bind to two or more polyether, poly (vinyl ester) and/or poly (vinyl alcohol) chains and include, for example, pentaerythritol triallyl ether.

Surfactant

The compositions of the invention may comprise a surfactant in addition to that required for the preparation of any PSA emulsion. The surfactants which are suitable for use in the compositions of the invention may be nonionic, cationic, anionic, zwitterionic or a mixture of such surfactants depending on the product form.

The hair styling compositions of the invention preferably comprise a non-ionic surfactant, in an amount of up to 5%, preferably from 0.01% to 1%, most preferably from 0.02% to 0.8% by weight based on total weight.

Examples of suitable non-ionic surfactants are condensation products of aliphatic ($C_8$-$C_{18}$) primary or secondary linear or branched chain alcohols or phenols with alkylene oxides, usually ethylene oxide and generally having at least 15, preferably at least 20, most preferably from 30 to 50 ethylene oxide groups. Other suitable non-ionics include esters of sorbitol, esters of sorbitan anhydrides, esters of propylene glycol, fatty acid esters of polyethylene glycol, fatty acid esters of polypropylene glycol, ethoxylated esters and polyoxyethylene fatty ether phosphates.

Of particular use are those non-ionic surfactants of general formula $R(EO)_xH$, where R represents a straight or branched chain alkyl group having an average carbon chain length of 12-18 carbon atoms and x ranges from 30 to 50. Specific examples include steareth-40, steareth-50, ceteareth-30, ceteareth-40, ceteareth-50 and mixtures thereof. Suitable commercially available examples of these materials include Unicol SA-40 (Universal Preserv-A-Chem), Empilan KM50 (Albright and Wilson), NONION PS-250 (Nippon Oils & Fats), Volpo CS50 (Croda Inc), and Incropol CS-50 (Croda Inc).

Water

Compositions of the present invention can also include water, preferably distilled or de-ionised, as a carrier for the PSAs, when used in an emulsion form in addition to it being a carrier or a solvent for other components. When present the water will typically be present in amounts ranging from 30% to 98%, preferably from 50% to 95% by weight.

Solvent/Carrier

Compositions of the present invention can also include solvents, as a carrier or solvent for the PSAs and other components. When present the solvent will typically be present in amounts ranging from 30% to 98%, preferably from 50% to 95% by weight. Examples of solvents are hydrocarbons, esters, alcohols etc.

Hair Conditioning Agents

Hair conditioning agents such as hydrocarbons, esters, silicone fluids, and cationic materials may be included in the compositions of the invention. Hair conditioning agents may typically be present in compositions of the invention in amounts of from 0.001% to 10% by weight, preferably 0.1% to 3% by weight. Hair conditioning agents may be single compounds or mixtures of two or more compounds from the same class or different general classes.

Hair conditioning agents may be included in any of the compositions of the invention, regardless of whether they contain a hair styling polymer. In one embodiment of the invention, the compositions (such as aerosol mousse formulations, for example) comprise a hair conditioning agent and are substantially free of hair styling polymer.

Suitable hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof.

Suitable oily or fatty materials are selected from hydrocarbon oils, fatty esters and mixtures thereof. Straight chain hydrocarbon oils will preferably contain from about 12 to about 30 carbon atoms. Also suitable are polymeric hydrocarbons of alkenyl monomers, such as $C_2$-$C_6$ alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used.

Suitable fatty esters are characterised by having at least 10 carbon atoms, and include esters with hydrocarbyl chains derived from fatty acids or alcohols, Monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as $C_1$-$C_{22}$ carboxylic acids. Preferred materials include cocoa butter, palm stearin, sunflower oil, soyabean oil and coconut oil.

Especially preferred is isopropyl myristate.

The oily/fatty material is suitably present at a level of from 0.05 to 10, preferably from 0.2 to 5, more preferably from about 0.5 to 3 wt %.

Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines, such as cetyl ammonium chloride, for example.

Compositions according to the invention may, optionally, comprise from 0.1% to 10% by weight of a volatile silicone as the hair conditioning agent. Volatile silicones are well known in the art and are commercially available and include, for example linear and cyclic compounds. Volatile silicone oils are preferably linear or cyclic polydimethylsiloxanes containing from about three to about nine silicon atoms.

The compositions of the invention may optionally comprise a cross-linked silicone polymer.

The cross-linked silicone polymer is preferably a non-rigid emulsion-polymerised and may be present in compositions of the invention in an amount of up to 10% by weight based on the total weight of the composition, more preferably from 0.2% to 6% by weight, most preferably from 0.5 to 5% by weight.

Preferred silicone polymers for use in the invention are polydiorganosiloxanes, preferably derived from suitable combinations of $R_3SiO_{0.5}$ units and $R_2SiO$ units where each R independently represents an alkyl, alkenyl (e.g., vinyl), alkaryl, aralkyl, or aryl (e.g. phenyl) group. R is most preferably methyl.

The preferred silicone polymers of the invention are cross-linked polydimethyl siloxanes (which have the CTFA designation dimethicone), and cross-linked polydimethyl siloxanes having end groups such as hydroxyl (which have the CTFA designation dimethiconol). Good results have been obtained with cross-linked dimethiconol.

Cross-linking of the silicone polymer is typically introduced concurrently during emulsion polymerisation of the polymer through the inclusion of the required amount of trifunctional and tetrafunctional silane monomer units, for example, those of formula:

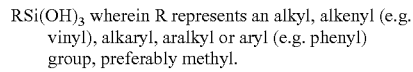

$RSi(OH)_3$ wherein R represents an alkyl, alkenyl (e.g. vinyl), alkaryl, aralkyl or aryl (e.g. phenyl) group, preferably methyl.

The degree of cross-linking of the silicone polymer can be measured as the percentage of branched monomer units in the silicone polymer and is from 0.05% to 10%, preferably being in the range 0.15% to 7%, e.g. from 0.2% to 2%. Increasing cross-linking is found to improve styling benefits but also to reduce conditioning performance somewhat, so compromise levels must be selected with properties optimised to suit consumer preferences in different cases. Good overall performance has been obtained with dimethiconol 0.3% cross-linked.

Suitable emulsion polymerised cross-linked silicone polymers are commercially available or can be readily made using conventional techniques well known to those skilled in the art.

Cross-linked silicone polymers are described in EP 818190, the contents of which are incorporated herein by reference.

The compositions of the invention may optionally comprise cationic surfactants, used singly or in admixture.

Cationic surfactants useful in compositions of the invention contain amino or quaternary ammonium hydrophilic moieties, which are positively charged when, dissolved in the aqueous composition of the present invention.

Examples of suitable cationic surfactants are those corresponding to the formula:

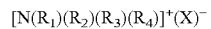

$[N(R_1)(R_2)(R_3)(R_4)]^+(X)^-$ in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention are monoalkyl quaternary ammonium compounds in which the alkyl chain length is C8 to C14.

Suitable examples of such materials correspond to the formula:

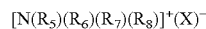

$[N(R_5)(R_6)(R_7)(R_8)]^+(X)^-$ in which $R_5$ is a hydrocarbyl chain having 8 to 14 carbon atoms or a functionalized hydrocarbyl chain with 8 to 14 carbon atoms and containing ether, ester, amido or amino moieties present as substituents or as linkages in the radical chain, and $R_6$, $R_7$ and $R_8$ are independently selected from (a) hydrocarbyl chains of from 1 to about 4 carbon atoms, or (b) functionalized hydrocarbyl chains having from 1 to about 4 carbon atoms and containing one or more aromatic, ether, ester, amido or amino moieties present as substituents or as linkages in the radical chain, and X is a salt-forming anion such as those selected from halogen, (e.g. chloride, bromide), acetate, citrate, lactate, glycolate, phosphate nitrate, sulphate, and alkylsulphate radicals.

The functionalised hydrocarbyl chains (b) may suitably contain one or more hydrophilic moieties selected from alkoxy (preferably $C_1$-$C_3$ alkoxy), polyoxyalkylene (preferably $C_1$-$C_3$ polyoxyalkylene), alkylamido, hydroxyalkyl, alkylester, and combinations thereof.

Preferably the hydrocarbyl chains $R_1$ have 12 to 14 carbon atoms, most preferably 12 carbon atoms. They may be derived from source oils which contain substantial amounts of fatty acids having the desired hydrocarbyl chain length. For example, the fatty acids from palm kernel oil or coconut oil can be used as a source of C8 to C12 hydrocarbyl chains.

Typical monoalkyl quaternary ammonium compounds of the above general formula for use in shampoo compositions of the invention include:

(i) lauryl trimethylammonium chloride (available commercially as Arquad C35 ex-Akzo); cocodimethyl benzyl ammonium chloride (available commercially as Arquad DMCB-80 ex-Akzo)

(ii) compounds of the formula:

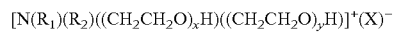

$[N(R_1)(R_2)((CH_2CH_2O)_xH)((CH_2CH_2O)_yH)]^+(X)^-$ wherein:

x+y is an integer from 2 to 20;

$R_1$ is a hydrocarbyl chain having 8 to 14, preferably 12 to 14, most preferably 12 carbon atoms or a functionalised hydrocarbyl chain with 8 to 14, preferably 12 to 14, most preferably 12 carbon atoms and containing ether, ester, amido or amino moieties present as substituents or as linkages in the radical chain;

$R_2$ is a $C_1$-$C_3$ alkyl group or benzyl group, preferably methyl, and

X is a salt-forming anion such as those selected from halogen, (e.g. chloride, bromide), acetate, citrate, lactate, glycolate, phosphate nitrate, sulphate, methosulphate and alkylsulphate radicals.

Suitable examples are PEG-n lauryl ammonium chlorides (where n is the PEG chain length), such as PEG-2 cocomonium chloride (available commercially as Ethoquad C12 ex-Akzo Nobel); PEG-2 cocobenzyl ammonium chloride (available commercially as Ethoquad CB/12 ex-Akzo Nobel); PEG-5 cocomonium methosulphate (available commercially as Rewoquat CPEM ex-Rewo); PEG-15 cocomonium chloride (available commercially as Ethoquad C/25 ex-Akzo)

(iii) compounds of the formula:

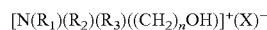

$[N(R_1)(R_2)(R_3)((CH_2)_nOH)]^+(X)^-$ wherein:

n is an integer from 1 to 4, preferably 2;

$R_1$ is a hydrocarbyl chain having 8 to 14, preferably 12 to 14, most preferably 12 carbon atoms;

$R_2$ and $R_3$ are independently selected from $C_1$-$C_3$ alkyl groups, and are preferably methyl, and $X^-$ is a salt-forming anion such as those selected from halogen, (e.g. chloride, bromide), acetate, citrate, lactate, glycolate, phosphate nitrate, sulphate, and alkylsulphate radicals.

Suitable examples are lauryldimethylhydroxyethylammonium chloride (available commercially as Prapagen HY ex-Clariant)

Mixtures of any of the foregoing cationic surfactants compounds may also be suitable.

Examples of suitable cationic surfactants include:

quaternary ammonium chlorides, e.g. alkyltrimethylammonium chlorides wherein the alkyl group has from about 8 to 22 carbon atoms, for example octyltrimethylammonium chloride, dodecyltrimethylammonium chloride, hexadecyltrimethylammonium chloride, cetyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallow trimethylammonium chloride, cocotrimethylammonium chloride, and the corresponding salts thereof, e.g., bromides, hydroxides. Cetylpyridinium chloride or salts thereof, e.g., chloride Quaternium –5

Quaternium –31

Quaternium –18 and mixtures thereof.

In the conditioners of the invention, the level of cationic surfactant is preferably from 0.01 to 10, more preferably 0.05 to 5, most preferably 0.1 to 2 wt % of the total composition.

Optional Conditioning Materials

Fatty Alcohol Material

Conditioner compositions of the invention preferably additionally comprise a fatty alcohol material. The combined use of fatty alcohol materials and cationic surfactants in conditioning compositions is believed to be especially advantageous, because this leads to the formation of a lamellar phase, in which the cationic surfactant is dispersed.

By "fatty alcohol material" is meant a fatty alcohol, an alkoxylated fatty alcohol, or a mixture thereof.

Representative fatty alcohols comprise from 8 to 22 carbon atoms, more preferably 16 to 20. Examples of suitable fatty Product Form Compositions of the present invention are formulated into hair styling compositions which may take a variety of forms, including, for example, mousses, gels, lotions, creams, sprays and tonics. These product forms are well known in the art.

The preferred product is a spray and/or aerosol and/or mousse.

The compositions of the invention are preferably foaming compositions. Foaming compositions are those compositions which are capable of forming a foam on dispensation from a suitable container, such as a pressurised aerosol container. More preferably are in the form of an aerosol hair mousse.

Aerosol-form compositions of the invention will include an aerosol propellant which serves to expel the other materials from the container, and forms the mousse character in mousse compositions. The aerosol propellant included in styling compositions of the present invention can be any liquefiable gas conventionally used for aerosol containers. Examples of suitable propellants include dimethyl ether and hydrocarbon propellants such as propane, n-butane and iso-butane. The propellants may be used singly or admixed. Water insoluble propellants, especially hydrocarbons, are preferred because they form emulsion droplets on agitation and create suitable mousse foam densities.

The amount of the propellant used is governed by normal factors well known in the aerosol art. For mousses the level of propellant is generally up to 35%, preferably from 2% to 30%, most preferably from 3% to 15% by weight based on total weight of the composition. If a propellant such as dimethyl ether includes a vapour pressure suppressant (e.g. trichloroethane or dichloromethane), for weight percentage calculations, the amount of suppressant is included as part of the propellant. For aerosol sprays the levels of propellant are usually higher; preferably from 30 to 98 wt % of the total composition, more preferably 50 to 95 wt %.

Preferred propellants are selected from propane, n-butane, isobutane, dimethyl ether and mixtures thereof. Preferably, the propellant comprises dimethyl ether and at least one of propane, n-butane and isobutane.

The method of preparing aerosol hair styling mousse compositions according to the invention follows conventional aerosol filling procedures. The composition ingredients (not including the propellant) are charged into a suitable pressurisable container which is sealed and then charged with the propellant according to conventional techniques.

Compositions of the invention may also take a non-foaming product form, such as a hair styling cream or gel. Such a cream or gel will include a structurant or thickener, typically at a level of from 0.1% to 10%, preferably 0.5% to 3% by weight based on total weight.

Examples of suitable structurants or thickeners are polymeric thickeners such as carboxyvinyl polymers. A carboxyvinyl polymer is an interpolymer of a monomeric mixture comprising a monomeric olefinically unsaturated carboxylic acid, and from about 0.01% to about 10% by weight of the total monomers of a polyether of a polyhydric alcohol. Carboxyvinyl polymers are substantially insoluble in liquid, volatile organic hydrocarbons and are dimensionally stable on exposure to air. Suitably the molecular weight of the carboxyvinyl polymer is at least 750,000, preferably at least 1,250,000, most preferably at least 3,000,000. Preferred carboxyvinyl polymers are copolymers of acrylic acid cross-linked with allylsucrose or allylpentaerythritol as described in U.S. Pat. No. 2,798,053. These polymers are provided by B.F. Goodrich Company as, for example, CARBOPOL 934, 940, 941 and 980. Other materials that can also be used as structurants or thickeners include those that can impart a gel-like viscosity to the composition, such as water soluble or colloidally water soluble polymers like cellulose ethers (e.g. methylcellulose, hydroxyethylcellulose, hydroxypropylmethylcellulose and carboxymethylcellulose), guar gum, sodium alginate, gum arabic, xanthan gum, polyvinyl alcohol, polyvinyl pyrrolidone, hydroxypropyl guar gum, starch and starch derivatives, and other thickeners, viscosity modifiers, gelling agents, etc. It is also possible to use inorganic thickeners such as bentonite or laponite clays.

The hair styling compositions of the invention can contain a variety of non-essential, optional components suitable for rendering the compositions more aesthetically acceptable or to aid use, including discharge from the container, of the product. Such conventional optional ingredients are well known to those skilled in the art, e.g. preservatives such as benzyl alcohol, methyl paraben, propyl paraben and imidazolidinyl urea, fatty alcohols such as cetearyl alcohol, cetyl alcohol and stearyl alcohol, pH adjusting agents such as citric acid, succinic acid, sodium hydroxide and triethanolamine, colouring agents such as any of the FD&C or D&C dyes, perfume oils, chelating agents such as ethylenediamine tetraacetic acid, and polymer plasticising agents such as glycerin and propylene glycol The invention will now be further illustrated by the following, non-limiting Examples.

Examples of the invention are illustrated by a number, comparative examples are illustrated by a letter.

The following PSA emulsions were used:

the PSA emulsions are defined below:

| | DC® 5-7300 | DC® 5-7200 | DC® 5-7200 | DC® 5-7200 |
|---|---|---|---|---|
| Product code | 18393-45 | 17724-65-A | 17724-65-B | 17724-65-C |
| % internal phase (solvent + PSA) | 60 | 60 | 60 | 60 |
| PSA:solvent ratio | 40:60 | 60:40 | 60:40 | 60:40 |
| Solvent | isododecane | 1 cSt PDMS | 1 cSt PDMS | 1 cSt PDMS |
| Resin:Polymer ratio | 65:35 | 65:35 | 65:35 | 55:45 |
| Particle size D50 (Microtrack) | 4.312 μm | 10 μm | 4 μm | 14 μm |
| Emulsifier | anionic | anionic | anionic | anionic |

Aerosol Mousse Example 1

| Ingredient | Trade Name | Raw Material Supplier | % wt. raw material |
|---|---|---|---|
| PSA emulsion | DC® 5-7200 17724-65-A | DOW CORNING | 2.8 |
| Cetearyl alcohol | LAUREX CS | ALBRIGHT & WILSON | 0.64 |
| Behenyl trimethyl ammonium chloride | GENAMIN KDMP | CLARIANT | 0.32 |
| Isopropyl myristate | ISOPROPYL MYRISTATE | UNIQEMA | 2 |
| Polyoxyethylene (10) lauryl ether | EMALEX 710 | NIHON EMULSION CO., LTD | 1 |
| Propane/Butane gas | CAP 40 | CALOR GAS | 8 |
| Water | DEIONISED WATER | Local supply | Up to 100 |

Aerosol Mousse Example 2

| Ingredient | Trade Name | Raw Material Supplier | % wt. raw material |
|---|---|---|---|
| PSA emulsion | DC® 5-7200 17724-65-B | DOW CORNING | 2.8 |
| Cross-linked methyl-polysiloxane | DOW CORNING 2-1787 HVF EMULSION | DOW CORNING | 2.8 |
| Methyl-polysiloxane emulsion (1MMcs) | DOW CORNING 2-1784 HVF EMULSION | DOW CORNING | 2 |
| Polyoxyethylene (10) lauryl ether | EMALEX 710 | NIHON EMULSION CO., LTD | 1 |
| Dimethyl ether | DYMEL A | DUPONT | 2 |
| Propane/Butane gas | CAP 40 | CALOR GAS | 6 |
| Water | DEIONISED WATER | Local supply | Up to 100 |

Cream/Lotion Example 3

| Ingredient | Trade Name | Raw Material Supplier | % wt. raw material |
|---|---|---|---|
| PSA emulsion[1] | DC ® 5-7200 17724-65-C | DOW CORNING | 2.8 |
| Cetearyl alcohol | LAUREX CS | ALBRIGHT & WILSON | 0.64 |
| Behenyl trimethyl ammonium chloride | GENAMIN KDMP | CLARIANT | 0.32 |
| Isopropyl myristate | ISOPROPYL MYRISTATE | UNIQEMA | 2 |
| Cationic acrylic homopolymer dispersed in an emollient ester | SALCARE SC96 | ALLIED COLLOIDS | 1.2 |

Feel Performance

The Test 18 trained panellists used the both prototype formulations and a control in duplicate for three days each in their homes and have scored the products using a 100 point scale on a number of attributes including stickiness of hair and stickiness of hand.

| Ingredient | Trade Name | Raw Material Supplier | 4 % wt. active ingredient | A % wt. active ingredient |
|---|---|---|---|---|
| DC ® 5-7200 17724-65-B | — | DOW CORNING | 1.7 | |
| Copolymer of 3-methyl-1-vinyl-1H-imidazolium chloride and 1-vinyl-2pyrrolidone (50:50) | Luviquat* FC550 | BASF PLC | | 2 |
| Cetearyl alcohol | LAUREX CS | ALBRIGHT & WILSON | 0.6 | 0.6 |
| Behenyl trimethyl ammonium chloride | GENAMIN KDMP | CLARIANT | 0.3 | 0.3 |
| Isopropyl myristate | ISOPROPYL MYRISTATE | UNIQEMA | 2 | 2 |
| Polyoxyethylene (10) lauryl ether | EMALEX 710 | NIHON EMULSION CO., LTD | 1 | 1 |
| Propane/Butane gas | CAP 40 | CALOR GAS | 8 | 8 |
| Water | DEIONISED WATER | Local supply | Up to 100 | Up to 100 |

Test Protocol Details

The panellists typically apply 5 g of product to their hair. They typically wash their hair every night and apply the mousse to their hair the following morning following their usual styling routine. The panellists used each product for 3 consecutive days and scored it on the third day using the score-sheet provided. Once all mousses have been evaluated in the order set out the test is completed.

Results

| | Normalised average scores* (%) | |
|---|---|---|
| | 4 | A |
| Stickiness of hand | −9 | 16 |
| Stickiness of hair | 3 | 9 |
| Volume down | 8 | 6 |

Example 4 gives similar volume control to comparative Example A, but it is perceived as less sticky on hair and much less sticky on hands.

Styling Performance

The styling performance of two PSA emulsions was compared to that of Luviquat* FC550 a conventional styling polymer.

A set of 5 2 g/25 cm switches made from 'virgin' Spanish hair was washed with 16% wt. SLES.2EO. 1 ml solution was applied along the length of the hair and agitated for 30 sec. The switches were then rinsed with warm water for 30 sec. Further 1 ml surfactant solution was applied and the hair was agitated for 30 sec again followed by 1 min rinse with warm water.

The towel dried hair was then treated with the Examples exemplified below:

| | | | % active ingredient | | |
|---|---|---|---|---|---|
| | | | B | 5 | 6 |
| Copolymer of 3-methyl-1-vinyl-1H-imidazolium chloride and 1-vinyl-2pyrrolidone (50:50) | Luviquat* FC550 | BASF PLC | 1.2 | | |
| PSA emulsion | DC ® 5-7200 17724-65-A | DOW CORNING | | 1.2 | |
| PSA emulsion | DC ® 5-7300 18393-45 | CALOR GAS | | | 1.2 |
| Polyoxyethylene (10) lauryl ether | EMALEX 710 | NIHON EMULSION CO., LTD | 1 | 1 | 1 |
| Propane/Butane gas | CAP40 | CAP 40 | 8 | 8 | 8 |
| Water | | LOCAL SUPPLY | Up to 100 | Up to 100 | Up to 100 |

1 g of mousse was applied to each set of 5 2 g/25 cm hair switches ensuring even distribution. Each switch was wound on a pegboard. The pegboards were then placed in a drying cabinet@65° C./10% RH for 3 h. Prior removing the curls, the pegboards were left at ambient conditions for 30 min. The curls were then hung on a panel and placed in humidity chamber at 30° C./90% RH. The curls were photographed every 5 min and a record of the curl length was kept.

The generated colour digital images were rendered into grey-scale format. The grey-scale images were subsequently converted into a binary form (i.e. composed only of black and white pixels). The dimensionless 2D projection area of each switch was used as a measure for the extent of switch spread out (i.e. loss of curliness). The projection area was calculated from the number of black pixels. The data were normalised by taking the ratio of the projection area to the average switch projection area calculated for the set of switches treated with Example 6.

|  | B | 5 | 6 | water |
|---|---|---|---|---|
| Normalised projection area after 1 h & 30° C./ 90% RH | 1.34 ± 0.13 | 1.27 ± 0.13 | 1 | 2.2 + 0.13 |

The pressure sensitive adhesives give similar or better curl retention to that of the styling polymer.

The styling performance of pressure sensitive adhesive emulsion was tested against conventional conditioning silicone and x-linked silicone used in styling formulations.

|  |  |  | % active ingredient | | |
|---|---|---|---|---|---|
|  |  |  | 7 | C | D |
| PSA emulsion | DC ® 5-7200 17724-65-A | DOW CORNING | 1.2 | | |
| Methylpolysiloxane emulsion (1MMcs) | DOW CORNING 2-1784 HVF EMULSION | DOW CORNING | | 1.2 | |
| Cross-linked methylpolysiloxane | DOW CORNING 2-1787 HVF EMULSION | DOW CORNING | | | 1.2 |
| Polyoxyethylene (10) lauryl ether | EMALEX 710 | NIHON EMULSION CO., LTD | 1 | 1 | 1 |
| Propane/Butane gas | CAP40 | CAP 40 | 8 | 8 | 8 |
| Water |  | LOCAL SUPPLY | Up to 100 | Up to 100 | Up to 100 |

Three sets of 5 2 g/25 cm 'virgin' Spanish hair were washed and treated with formulations 7, C and D as described above.

The switches were then hung vertically and left to dry@20° C./50% RH. The dried switches were photographed and the obtained images were analysed in the manner described above to obtain the average normalised projection area, which was used as a measure of the extent of switch expansion. Example 7 was used for control.

|  | 7 | C | D |
|---|---|---|---|
| Normalised projection area | 1 | 1.8 ± 0.1 | 3.6 ± 0.4 |

The pressure sensitive adhesive gives much lower hair volume than the conditioning and the styling silicone.

The invention claimed is:

1. A leave on hair treatment composition comprising propellant and a silicone pressure sensitive adhesive comprising
   a) from 40 to 70 parts by weight of at least one silicone copolymer resin; and
   b) 30 to 60 parts by weight of at least one polydiorganosiloxane
   wherein the at least one silicone copolymer resin comprises triorganosiloxy units of the formula $R_3SiO_{1/2}$ and tetrafunctional siloxy units of the formula $SiO_{4/2}$ and where in the at least one polydiorganosiloxane comprises ARSiO units terminated with end blocking $TRASiO_{1/2}$ units, and wherein each A is selected from radicals R or halo hydrocarbon radicals of 1-6 carbon atoms, and each T radical is R, OH, H or OR', wherein R' radical is an alkyl radical of 1-4 carbon atoms and wherein R in any of the above is independently a monovalent hydrocarbon radical of 1-6 carbon atoms, wherein the pressure sensitive adhesive is in the form of an emulsion and wherein the hair treatment composition is in the form of an aerosol mousse.

2. A hair treatment composition according to claim 1 in which the propellant is a hydrocarbon gas.

3. A hair treatment composition according to claim 1 further comprising a hair conditioning agent.

4. A composition according to claim 1, wherein the emulsion comprises a disperse solvent phase in a continuous water phase in the presence of a surfactant.

5. A composition according to claim 4, wherein the solvent has a boiling point below 300° C.

6. A composition according to claim 4, wherein the solvent comprises silicone.

7. A composition according to claim 4, wherein the dispersed solvent phase comprises 20 to 80% by weight of the silicone pressure sensitive adhesive.

8. A method for styling hair which comprises contacting the hair with a leave on hair treatment composition in accordance with claim 1.

* * * * *